(12) United States Patent
Weber et al.

(10) Patent No.: US 8,550,985 B2
(45) Date of Patent: Oct. 8, 2013

(54) APPLICATIONS OF LIPSS IN POLYMER MEDICAL DEVICES

(75) Inventors: Jan Weber, Maple Grove, MN (US); Tom Holman, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2653 days.

(21) Appl. No.: 11/011,454

(22) Filed: Dec. 14, 2004

(65) Prior Publication Data

US 2006/0173421 A1    Aug. 3, 2006

(51) Int. Cl.
*A61B 1/04*    (2006.01)
*A61B 1/00*    (2006.01)
*A61M 31/00*    (2006.01)
*A61M 37/00*    (2006.01)

(52) U.S. Cl.
USPC ............ 600/115; 600/116; 604/103.08

(58) Field of Classification Search
USPC .... 604/96.01, 101.01, 103.08; 600/115–116, 600/139
See application file for complete search history.

(56) References Cited

U.S. PATENT DOCUMENTS

| | | | |
|---|---|---|---|
| 4,931,384 A | 6/1990 | Layton et al. | |
| 4,994,033 A * | 2/1991 | Shockey et al. | 604/101.02 |
| 5,112,900 A | 5/1992 | Buddenhagen et al. | 524/484 |
| 5,348,538 A | 9/1994 | Wang et al. | 604/96 |
| 5,403,340 A | 4/1995 | Wang et al. | 606/194 |
| 5,447,497 A | 9/1995 | Sogard et al. | 604/101 |
| 5,473,138 A | 12/1995 | Singh et al. | |
| 5,549,552 A | 8/1996 | Peters et al. | 604/96 |
| 5,550,180 A | 8/1996 | Elsik et al. | 524/430 |
| 5,556,383 A | 9/1996 | Wang et al. | 604/96 |
| 5,737,126 A | 4/1998 | Lawanty | 359/620 |
| 5,826,588 A | 10/1998 | Forman | 128/898 |
| 5,830,182 A | 11/1998 | Wang et al. | 604/96 |
| 5,951,941 A | 9/1999 | Wang et al. | 264/523 |
| 5,980,564 A | 11/1999 | Stinson | |
| 6,010,480 A | 1/2000 | Abele et al. | 604/96 |
| 6,146,356 A | 11/2000 | Wang et al. | 604/96 |
| 6,171,278 B1 | 1/2001 | Wang et al. | 604/96 |
| 6,171,327 B1 * | 1/2001 | Daniel et al. | 606/200 |
| 6,171,328 B1 | 1/2001 | Addis | 606/200 |
| 6,328,925 B1 | 12/2001 | Wang et al. | 264/512 |

(Continued)

FOREIGN PATENT DOCUMENTS

WO    WO 2004/041344    5/2004

OTHER PUBLICATIONS

Lu, X.M.; Lu,Q.H.;Yin,J.;Zhu,Z.K.;Wang,Z.G., Laser-Induced Periodic Surface Structure on a Polymer Surface: The Effect of a Prerubbing Treatment on the Surface Structure, Feb. 9, 2003, Journal of Polymer Science,vol. 41, No. 12, pp. 1273-1280 (2003).*

(Continued)

*Primary Examiner* — Alireza Nia
(74) *Attorney, Agent, or Firm* — Vidas, Arrett & Steinkraus, P.A.

(57) ABSTRACT

Medical devices have material that that has a laser induced periodic surface structure (LIPSS) pattern on at least a portion thereof. The LIPSS pattern is provided by exposing a material surface to a pulsed polarized laser energy fluence below the ablation threshold. The LIPSS pattern is useful for purposes such as reducing contact areas on sliding surfaces, increasing total surface area for adhesions, providing anisotropic reinforcement of a material layer or layers, and to provide multiple channels for directing cell growth.

19 Claims, 4 Drawing Sheets

(56) References Cited

U.S. PATENT DOCUMENTS

| | | | |
|---|---|---|---|
| 6,406,457 B1 | 6/2002 | Wang et al. | 604/96.01 |
| 6,428,559 B1 | 8/2002 | Johnson | 606/200 |
| 6,537,480 B1 * | 3/2003 | Becker et al. | 264/400 |
| 6,551,342 B1 | 4/2003 | Shen et al. | 606/200 |
| 6,656,203 B2 | 12/2003 | Roth et al. | 606/200 |
| 6,676,683 B1 | 1/2004 | Addis | 606/200 |
| 6,840,950 B2 * | 1/2005 | Stanford et al. | 606/200 |
| 2003/0125762 A1 | 7/2003 | Eidenschink | 606/194 |
| 2003/0153943 A1 | 8/2003 | Michael et al. | 606/200 |
| 2003/0183966 A1 | 10/2003 | Wang et al. | 264/40.1 |
| 2003/0195554 A1 | 10/2003 | Shen et al. | 606/200 |
| 2004/0086674 A1 | 5/2004 | Holman | 428/36.9 |
| 2004/0167564 A1 | 8/2004 | Fedie | 606/200 |
| 2004/0256769 A1 | 12/2004 | Walter | 264/400 |

OTHER PUBLICATIONS

T. Lippert and J.T. Dickinson, "Chemical and Spectroscopic Aspects of Polymer Ablation: Special Features and Novel Directions," Chem. Rev., 2003, 103, 453-485.

W.Y.Y. Wong, T.M. Wong, H. Hiraoka, "Polymer segmental alignment in polarized pulsed laser-induced periodic surface structures," Appl. Phys. A 65, 519-523 (1997).

M. Csete, S. Hild, A. Plettl, P. Ziemann, Zs. Bor, O. Marti, "The Role of Original Surface Roughness in Laser-Induced Periodic Surface Structure Formation Process on Poly-Carbonate Films," Thin Solid Films, 453-454 (2004) 114-120.

M. Csete, J. Kokavecza, Zs. Bora, O. Martib, "The Existence of Sub-Micrometer Micromechanical Modulation Generated by Polarized UV Laser Illumination on Polymer Surfaces," Materials Science and Engineering C 23 (2003) 939-944.

M. Li et al, "Periodic microstructure induced by 532 nm polarized laser illumination on poly(urethane-imide) film: orientation of the azobenzene chromophore," Applied Surface Science 193 (2002) 46-51.

R. Kemkemer, et al, "The determination of the morphology of melanocytes by laser-generated periodic surface structures," Materials Science and Engineering C 23 (2003) 437-440.

Csete et al., "Laser-induced periodic surface structures on different poly-carbonate films", Applied Physics A., 73, (2001), pp. 521-526.

Trtica et al., "Pulsed TEA CO2 laser surface modifications of silicon," Applied Surface Science, 205 (2003), pp. 336-342.

Tsutsumi et al., "Pulsed laser induced spontaneous gratings on a surface of azobenzene polymer", Applied Physics Letters, vol. 85, No. 20, Nov. 15, 2004, pp. 4582-4584.

* cited by examiner

APPLICATIONS OF LIPSS IN POLYMER MEDICAL DEVICES

BACKGROUND OF THE INVENTION

Lasers have long been used to form structures from polymer materials by ablation and fusion. In some cases curable formulations may have been cured by exposure to UV laser beams or by laser induced heating.

Recently, a new laser effect has been reported, laser-induced periodic surface structures (LIPSS). These structures are sub-micrometer sized patterns said to have been first reported in poly(butylene terephthalate) (PET) and polystyrene (PS) at 193 and 248 nm. The patterns that have been reported to date include linear waves, and regular dots, can be produced by exposing a thermoplastic substrate surface to a fluence of polarized light that is below the laser ablation threshold energy fluence.

Articles, the entire contents of all of which are incorporated herein by reference, describing the LIPSS procedure and the structures obtained include:

T. Lippert and J. T. Dickinson, "Chemical and Spectroscopic Aspects of Polymer Ablation: Special Features and Novel Directions," Chem. Rev., 2003, 103, 453-485;

W. Y. Y. Wong, T. M. Wong, H. Hiraoka, "Polymer segmental alignment in polarized pulsed laser-induced periodic surface structures," Appl. Phys. A 65, 519-523 (1997);

M. Csete, S. Hild, A. Plettl, P. Ziemann, Zs. Bor, O. Marti, "The Role of Original Surface Roughness In Laser-Induced Periodic Surface Structure Formation Process on Poly-Carbonate Films," Thin Solid Films, 453-454 (2004) 114-120;

M. Csete, J. Kokavecza, Zs. Bora, O. Martib, "The Existence Of Sub-Micrometer Micromechanical Modulation Generated By Polarized UV Laser Illumination On Polymer Surfaces," Materials Science and Engineering C 23 (2003) 939-944;

M. Li et al, "Periodic microstructure induced by 532 nm polarized laser illumination on poly(urethane-imide) film: orientation of the azobenzene chromophore," Applied Surface Science 193 (2002) 46-51: and R. Kemkemer, et al, "The determination of the morphology of melanocytes by laser-generated periodic surface structures," Materials Science and Engineering C 23 (2003) 437-440.

Applications of LIPSS techniques that have been mentioned include microelectronic devices and in attaching and orienting chemical or biological objects. The use of LIPSS in medical device structures is not believed to have been reported.

SUMMARY OF THE INVENTION

In one aspect the invention pertains to medical devices are provided which have a LIPSS pattern on at least a portion of a surface thereof. The LIPSS pattern is useful to reduce contact areas on sliding surfaces, to increase total surface area for adhesions, to provide anisotropic reinforcement of a surface layer or layers, to align cell or dendrite growth, and the like.

In another aspect the invention provides a method for patterning a polymeric surface of a medical device. The process includes the step of subjecting the surface to polarized pulsed laser irradiation at fluence levels below the ablation threshold. The patterns obtainable by the process include linear waves extending in a longitudinal, oblique or circumferential directions, and annular or polygonal patterns propagating from an expanding center.

DETAILED DESCRIPTION OF THE INVENTION

Figure 1:
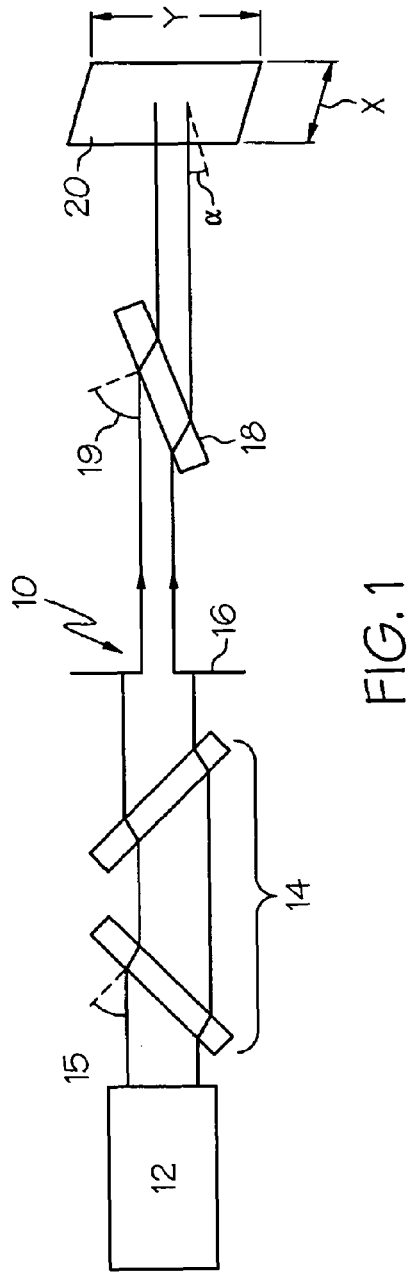
FIG. 1 shows schematically an apparatus for creating a LIPSS pattern on a surface.

The LIPSS effect uses polarized pulsed laser irradiation at fluence levels below the ablation threshold to create nanometer to single micron structures in the surface of polymers. The polymer is melted very briefly during the pulses, which are typically of nano-second duration. The electric field component of the laser light beam is oriented in a single direction because of the polarization of the beam, causing a small percentage of the polymer dipole segments of the polymer to align themselves with the field during the molten phase. Repeated laser pulsing gives an incremental effect and eventually causes a sufficient alignment of the polymer to produce a wave pattern, localized on the polymer surface that remains intact when laser irradiation is discontinued. By rotating the sample between the pulses, or series of pulses, a pattern of dots, rather than waves, can be formed on the surface. Instead of rotating the substrate, one could of course rotate the polarization vector by changing the orientation of the optical components.

A very strong film can be made by LIPSS patterning a film on both sides, the patterns being oriented at a crossing angle, for instance perpendicular, or by laminating multiple films with a LIPSS pattern thereon, the respective patterns crossing at different angles.

A UV wavelength that is highly absorbed by the particular polymer is suitably employed to generate the LIPSS pattern.

The period of the LIPSS is in the sub-micrometer region, and the line-shaped structures are parallel to the direction of polarization. The period of the LIPSS wave is typically in the order of magnitude of the laser wavelength, and depends on the illumination conditions and on the physical parameters of the material in accordance with formula (I) discussed below. The range of fluences effective for producing LIPSS features will vary according to the polymer material and the wavelength of the polarized laser light. In the case of PET, for instance, the range may be about 3-5 mJ cm$^{-2}$ at 193 nm for PET. The structure spacing is typically proportional to the laser wavelength, e.g., a spacing of 150 nm may be obtained on PET with 193 nm irradiation and of 190 nm for 248 nm irradiation. Similar conditions can also be used to generate LIPSS on polycarbonate (e.g. using a ArF excimer laser light (193 nm), "p" or "s" polarized, fluence of 4 mJ/cm$^2$, 800-1000 pulses, 30°-45° angle of incidence). LIPSS patterns on PET, polyimide, polystyrene and polysulfone can be obtained using the 4$^{th}$ harmonic of a Nd:YAG laser (266 nm) lasing at 10 Hz using a fluence of about 2 mJ/cm$^2$, 50° angle of incidence. In some cases a fluence of up to 10 mJ/cm$^2$, or even more, may be suitable. The depth of the pattern is determined by the laser energy applied.

Beam scattering by surface inhomogeneity can affect the LIPSS period and pattern. In general therefore a substantially uniform surface is desirable. However, if desired in a particular instance, an asymmetrical pattern in the topography can be deliberately obtained by manipulation of the initial surface roughness of the polymer material.

The LIPSS pattern can be distributed over the surface using beam scanning or substrate motion, or both. Laser energy can also be distributed over a large area using diffractive elements. Using holographic diffractors, one can establish almost any energy distribution. Substrate motion may be rotation or translation or both. Translation may be in one or both of x and y directions. Complex patterns can be obtained by periodically changing the orientation of the substrate relative to the beam or by changing the diffraction pattern of the beam. Dot patterns may be obtained by incremental rotation in the substrate plane between series of laser pulses, for instance every 10-100 pulses.

Applied atomic force microscopy, operating in Pulsed Force Mode, can be employed for analysis of the laser modified surfaces. Polarized reflected FT-IR can also be used to study dichroism of a LIPSS surface.

Although the applied laser fluence is well below the ablation threshold, some chemical changes to the polymer material may occur, particularly if the sample is exposed to air or oxygen during irradiation. If surface oxidization is undesirable, irradiation may be conducted while the substrate is flooded with nitrogen or inert gas or is in a vacuum.

The wave pattern is a function of the light wavelength and the angle of incidence of the laser beam and the material properties. For a given material the function is expressed by the formula (I):

$$\Pi = \frac{\lambda}{n \pm \sin\Theta} \quad (I)$$

where $\Pi$ is the period, n is the refractive index between the two media encountered as the beam is reflected off the surface, $\lambda$ is the wavelength and $\theta$ is the angle of incidence. The refractive index is typically taken between air and the polymer material, but may be different if an inert gas is provided or if the LIPSS pattern is built at an internal surface, i.e. by reflecting the beam off a boundary between two polymer layers.

LIPSS oriented PET surfaces have wave ridges that are significantly stiffer than the valleys. This is understood to be generally applicable to a wide variety of thermoplastic polymer materials, including semi-crystalline polymers and block copolymers and even largely amorphous thermoplastics, as aligned polar regions are more resistant to re-melting than adjacent amorphous regions.

Additionally, many thermoset materials that are gelled, but not fully cured, can be oriented by a LIPSS procedure. Thermoset materials include compositions that cure by application of heat, by mixing of chemically different ingredients or by exposure to radiation. For a gelled thermoset layer, subsequent LIPSS patterning followed by overfilling with successive top-layers of thermoset gel, each time LIPSS patterning the new top layers will create a multilayered oriented crystal structure throughout the bulk of the resulting polymer material. If at the same time the polarization of the laser is changed for some layers, or each layer, the crystals will be transverse in the planes defined by the changed angle layers, adding further to the overall strength of the material.

Suitably the most homogeneous part of the laser beam may be linearly polarized by a thin layer polarizer coated for the specific wavelength, the fluence is adjusted to between 0.5 and 10 mJ/cm$^2$ by applying an attenuator module.

Referring to FIG. 1, there is shown an apparatus 10 for producing a LIPSS pattern on a polymer surface substantially as shown in M. Csete, "The Role of Original Surface Roughness In Laser-Induced Periodic Surface Structure Formation Process on Poly-Carbonate Films," Thin Solid Films 453-454 (2004), p. 115. The device comprises a laser 12, for instance an ArF laser; an attenuator 14, the angle 15 of which is variable from 0 to 45°; an aperture 16, for instance providing a beam width of 5 mm; and a polarizer 18 for instance a Laseroptik thin layer polarizer producing "s" polarization. The polarizer angle 19 may be for instance about 70°. The sample 20 is mounted on a table not shown which allows the angle of incidence a to be varied and the sample to be translated in both the x and y directions. Of course equivalent mirror optics may be substituted for some or all of the lens optics structures depicted in FIG. 1.

There are various useful applications to which the LIPSS effect may be beneficially exploited in medical devices.

The ridge structure of a LIPSS pattern and relative hardness of the peaks can be used to reduce the contact area friction between two sliding polymer surfaces. By way of example, this property is beneficial for polymer cladding on guidewires, for the outer and inner surface of catheter tubes and endoscopes, and for the outer surface of balloons. There are several benefits here. Sliding resistance depends on actual contact area, and the total contact area of a surface is reduced to the area of the top of the ridges when a LIPSS pattern is produced. Furthermore, in a LIPSS pattern harder crystalline segments of the polymer are concentrated in the ridges. This allows relatively softer, more flexible bulk polymer to be used to form a device, but still obtain a surface in which the contact points are harder and tougher than the bulk material.

In addition to providing reduced sliding resistance due to reduced contact area, the hardened ridges of a LIPSS structured balloon outer wall can provide improved puncture resistance, e.g. by distributing puncture force along the more rigid ridges. This is particularly beneficial for balloons formed of polyester, polyetheretherketone (PEEK), polyamide or polyimide materials.

Although the wave or dot structure of a surface structured surface produces lower contact areas for sliding, the total area of the LIPSS surface is greater, when the area of the valleys is also taken into account. This can be exploited to increase interfacial adhesion when the surface is fully coated with an adhesive or biofunctional coating. The increased surface area can also be exploited to provide an increase in activity of thin functional bio-functional coatings, where activity is considered on the basis of the macroscopic area of the device.

Figure 2:
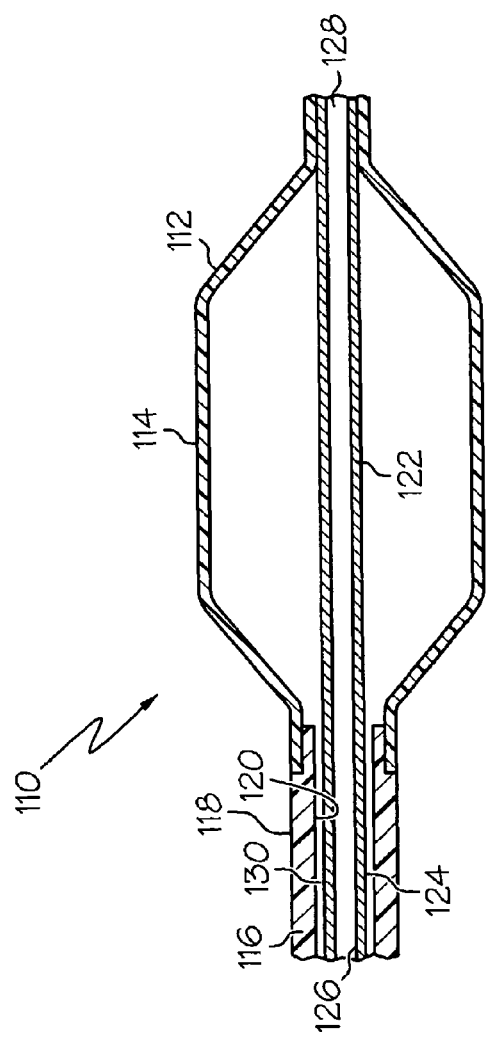
FIG. 2 is a side sectional view of a portion of a medical device of the invention.

In FIG. 2 there is distal segment of a balloon catheter 110 that includes a balloon 112 having an outer surface 114. Catheter 110 also includes an outer shaft 116 having outer and inner surfaces 118, 120, respectively, and in inner shaft 122 having outer and inner surfaces 124, 126, respectively. The inner shaft defines a guide wire lumen 128. The space between the inner and outer shafts defines an inflation lumen 130. The balloon 112 is bonded on its proximal end to the outer shaft 116 and on its distal side to the inner shaft 122.

Sliding surfaces of the catheter 110 include at least the inner surface 126 of the inner shaft 122, the outer surface 118 of the outer shaft 116, and the balloon outer surface 114. The inner surface 126 slides over a guide wire during deployment. Outer shaft surface 118 and a portion of the outer balloon surface 114 slide thorough the body vessel, for deployment and removal. In some cases the inner and outer shafts are made movable relative to each other so there may be sliding of inner shaft surface 126 relative to outer shaft surface 120.

In some embodiments of the present invention, the LIPSS surface modification may be repeated in successively applied polymer coating layers to build internal reinforcement at each layer interface, especially where the wave patterns of successive layers are aligned non-parallel.

Figure 3:
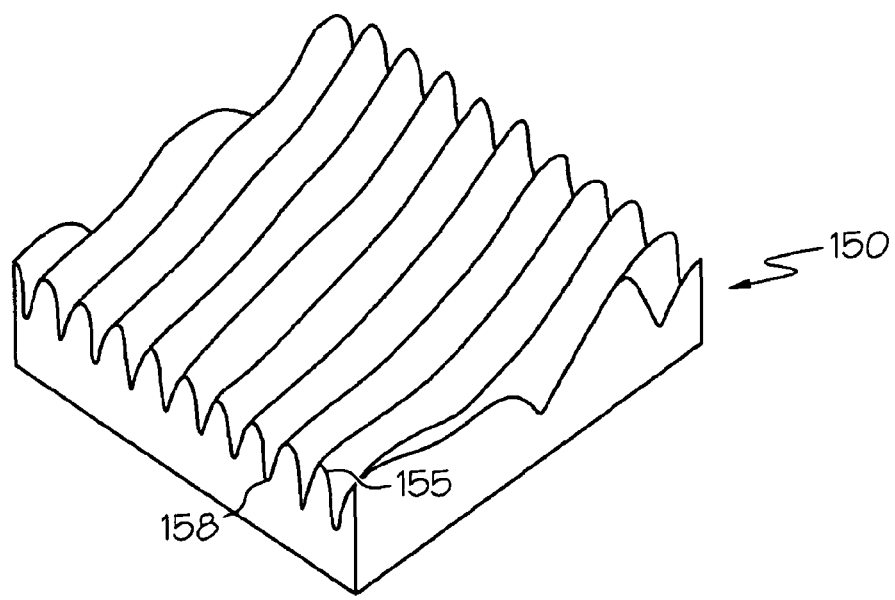
FIG. 3 is a magnified view of a fragment of a polymeric medical device surface having a stripe LIPSS pattern thereon.

FIG. 3 shows a magnified view of a fragment of a polymeric medical device surface 150 having a stripe LIPSS pattern thereon comprising peaks 155 and valleys 158. The periodicity of the pattern is in the range of 50-1000 nanometers, for instance 100-600 nm.

Figure 4:
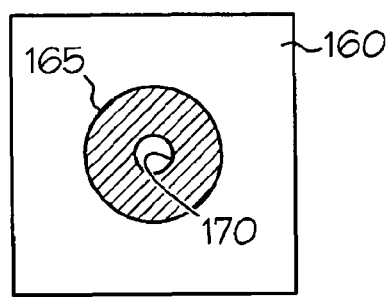
FIG. 4 is a schematic depiction of a fragment of a polymeric medical device surface having a dot area that has been inscribed with a crossing LIPSS pattern and which has a hole therethrough.

It is not necessary that a device surface be entirely patterned with the LIPSS. The LIPSS pattern may merely be provided at particular localities where reinforcement is desired. FIG. 4 schematically illustrates a fragment of a polymeric medical device surface 160 having dot area 165 that has been inscribed with a LIPSS pattern. The dot area 165 has a hole 170 extending through the surface. The hole 170 may be provided using the same laser apparatus, changing of angle of incidence toward perpendicular and an increasing the power to an ablation level. If the hole is used to pass material through the surface 160, the LIPSS pattern toughens the dot region 165 around the hole to reduce a tendency to enlarge during use. In an embodiment not shown, a crossing LIPSS pattern may be provided on the backside of the dot area 165.

Figure 5:
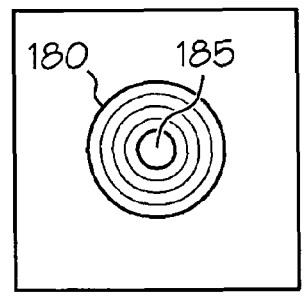
FIG. 5 is a view as in FIG. 4 in which an annular LIPSS pattern has been provided in the dot area.

Because LIPSS pattern correlates with the polarization of the laser beam, optical or mechanical manipulation of a beam can be employed to provide many alternative patterns other than a linear wave. For instance circular polarization can be used to produce annular waves, e.g. waves running in parallel with the circumference of a circular device or hole. FIG. 5 shows a configuration of a surface dot area 180 surrounding a hole 185, in which the LIPSS pattern on the surface of the dot 180 is annular. Polygonal patterns similarly can be produced by known optical techniques of beam splitting, bending and reflection.

Figure 6:
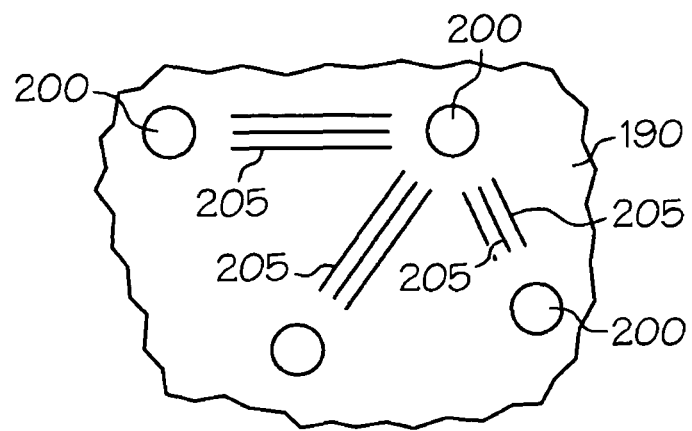
FIG. 6 illustrates a surface portion having a multiplicity of holes therethrough in which a stripe LIPSS pattern is provided between adjacent holes.
Figure 7:
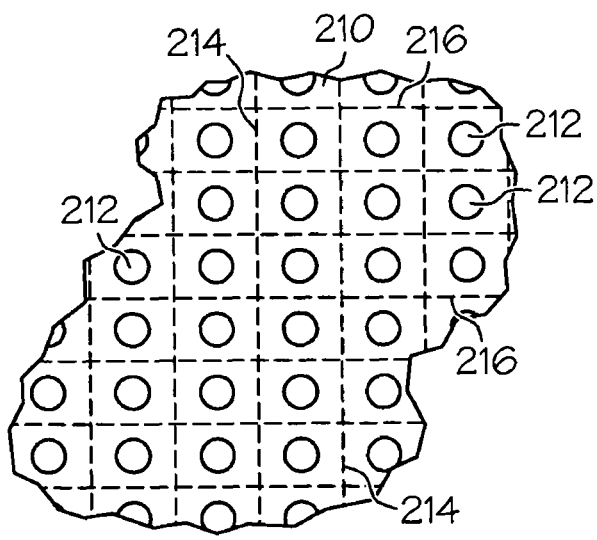
FIG. 7 illustrates a surface portion of a device having a multiplicity of holes therethrough with a crossing LIPSS pattern provided between the holes.

Surface reinforcement may also be provided between multiple holes in a substrate. FIG. 6 illustrates a surface portion 190 of a film substrate, having a multiplicity of holes 200 therethrough in which LIPSS wave patterns 205 are provided between adjacent holes 208. FIG. 7 illustrates an alternate surface portion 210 of a device having a multiplicity of holes 212 therethrough with crossing LIPSS patterns 214, 216 provided between the holes. In some cases LIPSS patterns disposed at crossing angles may be inscribed on opposite sides of the film substrate to maintain the continuity of the wave patterns.

Figure 8:
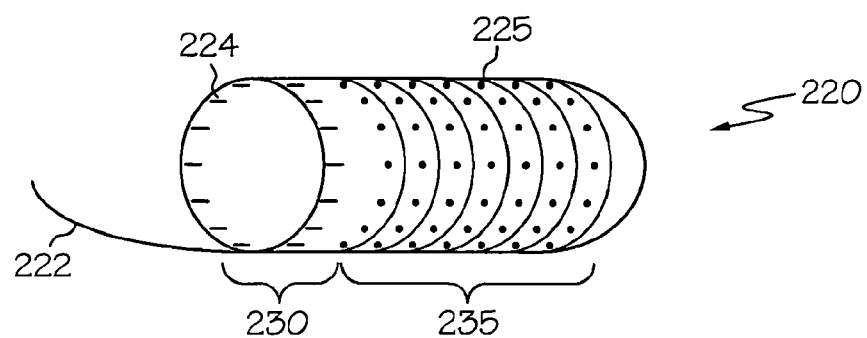
FIG. 8 is a schematic representation of a blood filter device for intravascular deployment, employing a filter membrane having a LIPSS pattern thereon.

The LIPSS pattern may be different on different portions of the device. FIG. 8 is a schematic representation of a blood filter device 220 for intravascular deployment during a surgical procedure such as catheter atherectomy to catch embolic material generated or released during the procedure. The device 220 comprises a wire 222, at the distal end of which is a loop 224 over which is attached a filter membrane in the form of a bag 225 having LIPSS patterns thereon. In the region 230 of the bag, near its overlap with the loop 220, the LIPSS pattern is longitudinal relative to the flow direction. In the region 235 of the bag a circumferential LIPSS pattern is provided. Alternatively, areas around the holes in region 235 may be patterned in any of the manners discussed with respect to FIGS. 4-7.

Figure 9:
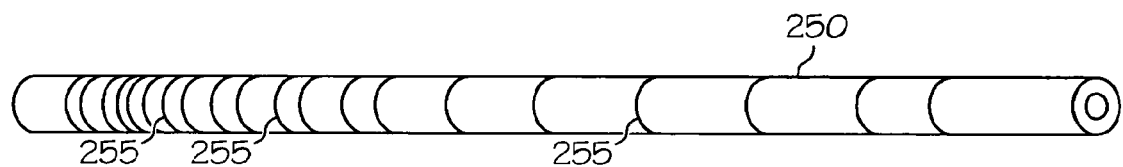
FIG. 9 illustrates a tubular member having a circumferential LIPSS pattern thereon of varying density.

FIG. 9 illustrates a tubular member 250 having circumferential LIPSS pattern waves 255 thereon. The waves 255 can be employed to increase burst resistance of the tube. The stripe pattern may be circular or spiral. Providing a pattern of stripes of varying density or angle along the length of the tube can be used to alter the flexibility of the tube along its length.

Figure 10:
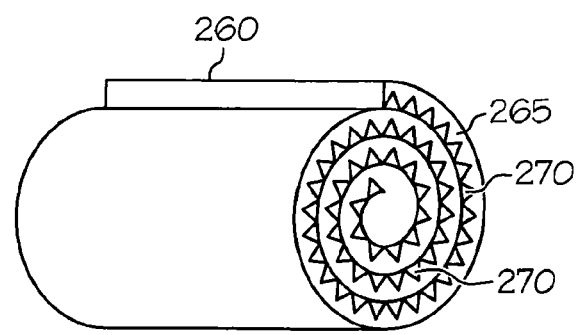
FIG. 10 illustrates a surface prepared by sectioning a roll of a film material having a stripe LIPSS pattern thereon.

The peak-to-peak spacing and peak-to-valley depth of LIPSS patterns can be employed to provide devices with channels of sizes specific sizes. FIG. 10 illustrates a device 260 prepared by rolling a film to provide layers 265. The film has a wave LIPSS pattern thereon. The film is rolled along a longitudinal axis that is generally parallel to the pattern. Suitably the roll is sectioned along planes that cross the longitudinal axis of the roll. The valleys of the LIPSS pattern provide channels 270 of closely controlled size that can be used for filtration. In some embodiments the smooth side of the film can be bonded to the tips of the peaks on the adjacent LIPSS surface. Adhesion may be provided by providing the smooth side of the film with a pressure sensitive or with a curable adhesive layer.

Roll sections of the type illustrated in FIG. 10 can also be used as an implant to channel dendrite growth of specific cell types, such as neurons. As an example, dendrite growth from healthy nerve tissue on either side of an injury site can be induced to grow through the individual channels to facilitate reestablishment of communication between individual neurons of the healthy tissue. In some cases it may effective to place nerve stem cells between roll segments to effect even longer range reconnection between healthy nerve tissues. To induce dendrite growth nerve growth factors may be provided in the channels. The polymer material of such an implant may be biodegradeable. A surgical method for treating a nervous system injury comprising implanting such a device at an injury site with the channels in the device extending between healthy neurons, or between stem cells and healthy neurons, constitutes a further aspect of the invention.

LIPSS produces a localized molecular alignment of specific polymer molecule portions. Therefore, with polymers having a substantial conductivity difference between polar and non-polar regions of the molecule, the LIPSS pattern can arrange conductive portions together. The electrical properties of the film surface thus can be varied to produce anisotropic conductivity. Devices can be produced that have specific localized electrical properties that can direct biologic activity. Electronic devices can also be built using multiple LIPSS patterned layers where there is a significant anisotropy in conductivity provided by the LIPSS.

Where an inner surface of a device such as a catheter tube is desired to be reformed by a LIPSS procedure, the laser energy may be delivered to the surface via an optical fiber.

Applications of the invention are seen for any tubular or wire-like surface where a durable low sliding friction surface is needed, especially where the thickness dimension of the device must be minimal. The LIPSS pattern may be on the outer surface, or an inner tubular surface, and it may be continuous or discontinuous.

A sliding surface of any medical device may be modified using the techniques described herein. The present invention finds particular utility for catheter assemblies. Catheter assemblies are employed in a wide range of procedures and are used for example, for procedures in vasculature (including coronary vasculature), in the biliary duct, in the neurological system, in the urinary tract, in the reproductive system, etc. as well as guide catheters and delivery systems for medical devices such as stent delivery systems. By way of non-limiting example, the present invention may be employed to modify catheter shaft inner or outer surfaces, as well as such surfaces of balloons. Stent sleeves or other stent protecting structures may also be advantageously provided with LIPSS features. Guide wires may also be advantageously coated with a polymer coating having a LIPSS induced wave or dot pattern to reduce sliding friction in the body and to reduce lumen friction when the catheter is passed over the wire.

The LIPSS pattern can also be advantageously employed on surfaces that must be peeled from contact with another. Some stent protection structures work in such a way. If opposing surfaces are provided with wave patterns that cross when the surfaces are mated, the contact adhesion at the interface of such surfaces can be reduced.

In general LIPSS patterns can be induced in thermoplastic polymer materials. Thermoset compositions that have gelled at the surface, or very close thereto, but have not yet been fully cured at the surface, may also be suitable substrates for formation of LIPSS patterns thereon. In some cases, the laser irradiation may be used to concurrently cure and form a LIPSS pattern thereon.

Examples of polymeric materials suitable for use herein include, but are not limited to, silicone resins, phenolic resins, polyolefins, polyvinyls, polyesters, polyacrylates, polyethers, polyamides including the nylons, polysulfones, cellulosic materials, polystyrene, polyisobutylene, polybutene, polyamide, polycarbonates, polyepoxides, polyacrylonitriles (PAN), block copolymers, etc., copolymers thereof, and mixtures thereof, as well as a wide variety of other polymeric materials not specifically mentioned herein. As used herein, the term "copolymer" refers to any polymer formed using two or more monomers, including terpolymers and so forth.

Examples of suitable polyolefins include polyethylene, polypropylene as well as copolymers thereof.

Examples of suitable polyester copolymers include, but are not limited to, polyethylene terephthalate, polybutylene terephthalate, polyethylene isophthalate, polyethylene naphthalate, polybutylene naphthalate and so forth.

Examples of polyamide materials include nylon 6, nylon 6/6, nylon 6/12, nylon 9/12, nylon 6/10, nylon 10, nylon 11, nylon 12, and the like.

Examples of polyether copolymers include polyetheretherketones (PEEK).

Examples of suitable styrenic block copolymers include, but are not limited to, those block copolymers having styrenic endblocks, including, but not limited to, styrene-isoprene-styrene (SIS), styrene-butadiene-styrene (SBS), styrene-ethylene/propylene-styrene (SEPS), styrene-isobutylene-styrene (SIBS), styrene-ethylene/butylene-styrene (SEBS), and so forth.

Examples of suitable polyamide block copolymers include, for example, the polyether-block-amides. Examples of polyester block copolymers include, but are not limited to, polyester-block-ester copolymers, polyester-block-ether copolymers and so forth. Polyester and polyamide block copolymer elastomers, and their use as balloon materials are also described in commonly assigned U.S. Pat. Nos. 6,406,457, 6,171,278, 6,146,356, 5,951,941, 5,830,182, 5,556,383, 5,112,900.

Examples of suitable polymeric materials particularly suited to forming medical balloons include, but are not limited to, polyesters and copolymers thereof; polyamides and copolymers thereof; polyamide block copolymers, such as those available under the tradename of PEBAX® available from Atofina Chemicals in Philadelphia, Pa.; polyester block copolymers, polyurethane block copolymers, polyolefins and copolymers thereof, and mixtures thereof. Poly(ester-block-ether) elastomers are available under the tradename of HYTREL® from DuPont de Nemours & Co. and consist of hard segments of polybutylene terephthalate and soft segments based on long chain polyether glycols. These polymers are also available from DSM Engineering Plastics under the tradename of ARNITEL®. Suitable balloon materials are also described in commonly assigned U.S. Pat. Nos. 5,549,552, 5,447,497, 5,348,538, 5,550,180, 5,403,340, 6,328,925, each of which is incorporated by reference herein in its entirety.

Particularly suitable polymeric materials for forming catheter shafts include, but are not limited to, polyolefins such as polyethylene, polyethylene terephthalate, polybutylene terephthalate, polyethylene naphthalate, poly(ether-block-amide), poly(ester-block-ether), poly(ester-block-ester), and so forth.

As examples of thermoset materials there are light and/or heat activated one-part acrylic, epoxy, vinyl ether and polythiol/polyene system, moisture activated polyisocyanate and silicones, and two-part acrylic, epoxy, silicon and polyurethane systems.

Multilayer structures may also be employed herein where two or more polymer layers are formed using the same or different polymeric compositions, with the light energy directed to reflect off of the interface between the two layers to produce LIPSS patterning at the interface.

In general it is preferred to use light wavelengths of lower energy, for instance in the near UV or visible region, to avoid side reactions that can occur with higher energy irradiation. If it is desired to use a wavelength for the LIPSS patterning step that is not strongly absorbed by a particular polymer, the polymer may be modified to incorporate a moiety that is strongly absorbed by light of the desired wavelength. An illustration of the technique of polymer modification is provided in M. Li et al, "Periodic microstructure induced by 532 nm polarized laser illumination on poly(urethane-imide) film: orientation of the azobenzene chromophore," Applied Surface Science 193 (2002) 46-51.

Catheters may be formed of conventional materials with constructions that are described in detail in the art. The proximal shaft section can be manufactured by multi-lumen extrusion using a high-strength polymer such as a polyolefin, polyalkylene terephthalate, nylon, poly(ether-block-amide), polyetheretherketone (PEEK), etc. Coextrusion can be employed to form a multilayer structure as well.

Fibrous material in the form of braiding, weaving, knitting, roving, random, etc. may be also provided within a layer, or between layers of the medical devices of the invention.

The LIPSS pattern may also be induced in an organometallic polymeric material that functions as a ceramic precursor. Further thermal treatment of the precursor can then produce ceramics that have a wavy or other pattern on the surface derived from the LIPSS pattern of the precursor. A further aspect of the invention therefore is a medical device comprising a portion of ceramic material obtained by thermal treatment of a polymeric material precursor, wherein the precursor had a laser induced periodic surface structure (LIPSS) pattern on at least a portion of a surface thereof or at an interface between two or more layers of material.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A medical device comprising a portion of material that has a laser induced periodic surface structure (LIPSS) pattern on at least a portion of a surface thereof or at an interface between two or more layers of material.

2. A medical device as in claim 1 wherein the material is a polymeric material.

3. A medical device as in claim 2 wherein the polymeric material is selected from the group consisting of silicone resins, phenolic resins, polyolefins, polyvinyls, polyesters, polyacrylates, polyethers, polyamides, polysulfones, cellulosic materials, polystyrene, polyisobutylene, polybutene, polyamide, polycarbonates, polyepoxides, polyacrylonitriles, copolymers of two or more thereof and blends of two or more thereof.

4. A medical device as in claim 2 wherein the polymeric material is a thermoplastic polymer.

5. A medical device as in claim 2 wherein the polymeric material is a thermoset material.

6. A medical device as in claim 1 wherein the device has at least one hole through the LIPSS patterned portion thereof.

7. A medical device as in claim 6 wherein the device is a filter membrane.

8. A medical device as in claim 1 wherein the device includes a tubular polymeric portion having an exterior surface and the LIPSS pattern is formed on at least a portion of said exterior surface.

9. A medical device as in claim 1 wherein the device includes a tubular polymeric portion having an interior lumen surface and the LIPSS pattern is formed on at least a portion of said interior lumen surface.

10. A medical device as in claim 1 wherein the LIPSS pattern is present at an interface between two or more layers of material, the device having surfaces extending transverse to the interface, and the LIPSS pattern providing a plurality of channels extending between said transverse surfaces.

11. A medical device as in claim 1 wherein the LIPSS pattern is annular or polygonal.

12. A medical device as in claim 1 further comprising a biofunctional material applied to at least a portion of the LIPSS patterned surface.

13. A medical device as in claim 1 wherein the device is selected from the group consisting of catheters, balloons, filters, implants for directing neural cell growth, stent placement devices, endoscopes and guide wires.

14. A medical device as in claim 1 wherein the LIPSS pattern is provided at successive interfaces between three or more successive layers of the same or different polymer material, a successive layer overfilling the LIPSS pattern of a preceding layer.

15. A medical device as in claim 14 wherein the polymer material is a thermoset.

16. A medical device as in claim 15 wherein the LIPSS patterns of at least two said successive layer interfaces are non-parallel.

17. A medical device that has two contacting surfaces wherein at least one of said two surfaces has a laser induced periodic surface structure (LIPSS) pattern thereon.

18. A medical device as in claim 17 wherein both said surfaces have a LIPSS pattern thereon.

19. A medical device for vascular access or surgery, the device comprising a tubular polymeric portion having interior and exterior surfaces, at least one of said surfaces having a laser induced periodic surface structure (LIPSS) pattern formed on at least a portion thereof.

* * * * *